United States Patent
Mottate et al.

[11] Patent Number: 5,947,723
[45] Date of Patent: Sep. 7, 1999

[54] TITANIUM ORTHODONTIC APPLIANCES

[75] Inventors: Mikio Mottate; Masaaki Orikasa, both of Ohkuma-machi; Kikuo Nishi, Haramachi, all of Japan

[73] Assignee: GAC International, INc., Central Islip, N.Y.

[21] Appl. No.: 08/054,927

[22] Filed: Apr. 28, 1993

[51] Int. Cl.⁶ .................................................. A61C 3/00
[52] U.S. Cl. .................................................................. 433/8
[58] Field of Search ............................. 433/8, 9, 10, 11, 433/12, 13, 14, 15, 16, 17, 18, 19, 20, 21, 23, 24

[56] References Cited

U.S. PATENT DOCUMENTS

| | | | |
|---|---|---|---|
| 4,082,900 | 4/1978 | Shimogori et al. | 428/469 |
| 4,197,643 | 4/1980 | Burstone et al. | 433/20 |
| 4,202,751 | 5/1980 | Fukuzuka et al. | 204/197 |
| 4,210,447 | 7/1980 | Tsai | 75/171 |
| 4,954,080 | 9/1990 | Kelly et al. | 433/8 |
| 5,017,133 | 5/1991 | Miura | 433/20 |
| 5,018,969 | 5/1991 | Andreiko et al. | 433/20 |
| 5,062,794 | 11/1991 | Miura | 433/10 |
| 5,064,369 | 11/1991 | Kawaguchi | 433/3 |
| 5,068,003 | 11/1991 | Takahashi et al. | 148/421 |
| 5,131,843 | 7/1992 | Hilgers et al. | 433/20 |
| 5,156,807 | 10/1992 | Nagata et al. | 420/417 |
| 5,232,361 | 8/1993 | Sachdera et al. | 433/8 |

FOREIGN PATENT DOCUMENTS

| | | |
|---|---|---|
| A0 359 446 | 3/1990 | European Pat. Off. . |
| WO 92/16159 | 10/1992 | WIPO .............................. A61C 7/00 |

OTHER PUBLICATIONS

Database WPI, Section Ch. Week 8748, Derwent Publications Ltd., London, GB; Class D22, An 87–339740 & JP–A–62 246 372 (Nippon Tungsten KK) Oct. 27, 1987 – abstract.

Chemical Abstracts, vol. 111, No. 26, Dec. 25, 1989, Columbus, Ohio; abstract No. 239425, Hamada, Tadashi et al., "Titanium–molybdenum–aluminum shape memory alloys as a biomaterial" –abstract.

J. Dent. Res. vol. 58, No. 2, Feb. 1979, J. Goldberg E.A. "An Evaluation of Beta Titanium Alloys for Use in Orthodontic Appliances".

Elvers et al., "Ullmann's Encyclopedia of Industrial Chemistry", 5th ed. 1990, Weinheim, Fed. Rep. of Germany, vol. B1, pp. 10–4 to 10–7.

*Primary Examiner*—Nicholas D. Lucchesi
*Attorney, Agent, or Firm*—Kenyon & Kenyon

[57] ABSTRACT

Orthodontic appliances formed of a titanium alloy which substantially avoids toxic or allergic reactions in patients containing a β-stabilizing element including at least 12 wt % molybdenum to produce a stable β-monophase at body temperature are disclosed. The yield strength of the titanium alloy is within the range 1150 to 1450 MPa. The tensile strength of the titanium alloy is within the range 1350 to 1950 MPa. The elongation of the titanium alloy is within the range 10 to 14%. The titanium alloy may also contain about 5 wt % zirconium as another β-stabilizing element. It may also contain about 3 wt % aluminum to improve age hardenability by strengthening the α-phase.

17 Claims, 2 Drawing Sheets

5,947,723

1

TITANIUM ORTHODONTIC APPLIANCES

FIELD OF THE INVENTION

The present invention relates to orthodontic appliances adapted in the field of orthodontics for moving teeth in a prescribed direction for the purpose of correcting irregularities of the teeth, and more particularly to orthodontic appliances made of a novel titanium alloy.

BACKGROUND OF THE INVENTION

Stainless steel has been the predominant alloy used in orthodontic appliances. However, the nickel component of stainless steel has a tendency to leach into saliva inside the oral cavity. This may cause harmful reactions, such as allergies and the like. Approximately one in every 200 to 300 patients are known to be allergic to nickel. Thus, there has been an effort to develop orthodontic appliances that do not contain nickel.

Recently, titanium has been considered as a substitute for stainless steel. However, the use of titanium in orthodontic appliances is not new. Titanium has been used not only in dental materials, but also in medical materials since the 1950s. Because of its affinity in vivo, titanium has been used in implants and artificial joints for years. Initially, pure titanium was used, but this was not always satisfactory because even the strongest grade had a yield strength of only 500 to 650 MPa (elongation 15%).

In applications involving stress and in parts where resistance is important, Ti-6Al-4V alloys have been used, these being α+β type titanium alloys. Among these, Ti-6Al-4V-ELI has often been used as a titanium alloy in vivo. Ti-6Al-4V-ELI alloy was originally developed as a refractory material by the aerospace engineering industry before being used in vivo. This alloy decreases elution of vanadium, aluminum and titanium molecules (corrosion in industrial applications) by suppressing impurities to an extremely low level. The 0.2% yield strength of Ti-6Al-4V-ELI is 800 MPa (elongation 6%) according to the ASTM Surgical Implant Standard. Such a yield strength is generally insufficient for use in current orthodontic appliances where the trend is toward miniaturization and higher yield strengths.

Currently, Ti-6Al-4V-ELI is considered the most proximate in vivo metal material. However, with this alloy there is still elution of metal ions caused by reactions with biologic saline water and organic acids in the oral cavity. The vanadium (V) component of the alloy even in minute amounts is an element that is non-degradable in the human body. Under increased local concentrations its valency increases together with oxidation which results in toxicity to the central nervous system as well as cell toxicity. Also, when the aluminum component increases in concentration because of bonding with inorganic phosphorus there is a deficiency of phosphorus in the blood and in bones.

U.S. Pat. No. 4,197,643 discloses orthodontic wires, for example, ligature wires and retaining wires, containing a β-titanium alloy having the components Ti-11.5Mo-6Zr-4Sn. The alloy had a rolled (mill processed) yield strength of $17.0 \times 10^4$ psi (1170 MPa), and after aging treatment (heat aged) for four hours at 900° F. (482° C.) had a yield strength of $20.1 \times 10^4$ psi (1385 MPa). 18-8 stainless steel data shown for comparison had $27.0 \times 10^4$ psi (1860 MPa). These properties are highly desirable in orthodontic wires such as ligature wires and retaining wires.

According to MIL standards, the 0.2% yield strength of Ti-11.5Mo-6Zr-4.5Sn in the annealed state is 620 MPa

2

(elongation 10%). Although the standard does not clearly and specifically indicate an alloy of this composition given aging treatment after solid solution treatment[1], it has on the order of 1200 MPa at 0.2% resistance and the tensile strength is on the order of 1300 MPa. Not only does an alloy of this composition not contain elements believed harmful to the human body, but it also falls generally in the range of strengths required for orthodontic appliances. However, a drawback of the Ti-11.5Mo-6Zr-4.5Sn β-titanium alloy composition is that it does not have a β-monophase that is stable at body temperature.

Solid solution treatment : STA=solution treated and aged. In this case "aged" is the same as precipitation hardening. Conditions indicated by the AMS standard are 690 to 730° C. and 690 to 745° C.

OBJECTS AND SUMMARY OF THE INVENTION

It is an object of the present invention to provide orthodontic appliances formed of a titanium alloy that has a high safety and is stable for long periods in vivo.

It is another object of the present invention to provide orthodontic appliances formed of a titanium alloy that has a high strength and elongation resistance.

It is a further object of the present invention to provide orthodontic appliances formed of a titanium alloy that does not cause cell toxicity problems.

It is another object of the present invention to provide orthodontic appliances formed of a titanium alloy that has a β-monophase that is stable at body temperature.

The present invention provides orthodontic appliances formed of a titanium alloy which substantially avoids toxic or allergic reactions in patients comprising a β-stabilizing element including at least 12 wt % molybdenum to produce a β-monophase that is stable at body temperature. The yield strength of the alloy is within the range 1150 to 1450 MPa, and its tensile strength is within the range 1350 to 1950 MPa. The elongation of the titanium alloy is within the range 10 to 14%. The titanium alloy may also comprise about 5 wt % zirconium as another β-stabilizing element. It may also comprise about 3 wt % aluminum to improve age hardenability by strengthening the α-phase. The orthodontic appliances of the present invention include but are not limited to brackets, archwires, expansion screws, buccal tubes and circular orthodontic bands.

An advantage of the titanium alloy of the present invention is that it does not cause allergic reactions or cell toxicity problems in patients.

Another advantage of the titanium alloy of the present invention is that it has a low coefficient of friction enabling enhanced tooth movement. It also has a high strength and elongation resistance which are particularly useful properties in orthodontic appliances which are becoming increasingly smaller.

A further advantage of the titanium alloy of the present invention is that it does not deteriorate in the mouth, has a high safety and is stable for long periods in vivo.

Other objects, characteristics, and advantages of the present invention will become apparent in view of the detailed description and accompany drawings that follow.

DETAILED DESCRIPTION

The present invention is directed to orthodontic appliances formed of a titanium alloy. The term "orthodontic appliance" is used herein in a broad sense to include any device intended for mounting on a tooth, and used to transmit to the tooth corrective force from an archwire, spring, elastic, or other activatable force-applying component. The term includes but is not limited to brackets, archwires, expansion screws, buccal tubes, circular orthodontic bands, and ligature wires.

Figure 1:
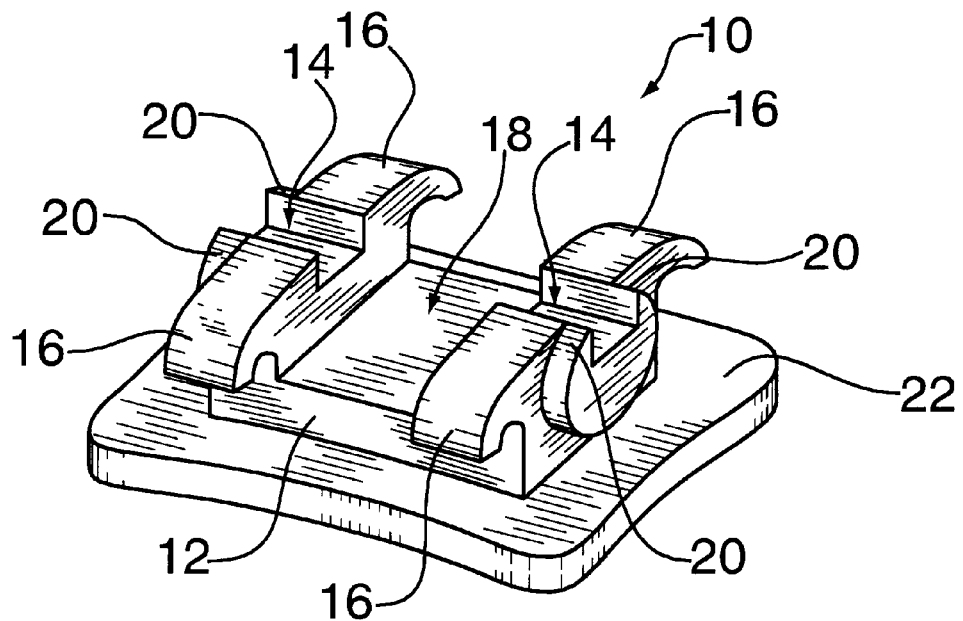
FIG. 1 is a perspective view of one embodiment of an orthodontic bracket formed of a titanium alloy according to the present invention.

FIG. 1 shows an exemplary orthodontic appliance 10 in the form of an orthodontic bracket. The orthodontic appliance 10 comprises a bracket portion 12, and a longitudinal archwire slot 14 formed in an upper surface of the bracket portion extending through the bracket portion in the mesial-distal direction thereof. The orthodontic appliance 10 is a twin tie-wing appliance and, therefore, includes two pairs of tie-wings 16. The tie-wings project outwardly from either side of the archwire slot 14. A channel 18 extends through the bracket portion 12 in a direction substantially perpendicular to the archwire slot 14, between the pairs of tie-wings 16.

The orthodontic appliance further comprises four shoulders 20 extending upwardly on the bracket portion 12 on the free end thereof, on either side of the archwire slot 14. Two opposing shoulders 20 are located on the mesial end of the orthodontic appliance 10, and the other two opposing shoulders 20 are located on its distal end. Each of the shoulders 20 includes a rounded exterior surface which extends upwardly on the bracket portion 12 and terminates on the top edge of the archwire slot 14. Each shoulder 20 is defined substantially by a radius of curvature.

The orthodontic appliance 10 further comprises a base member 22, fixed to the underside of the bracket portion 12, suitable for either direct bonding to a tooth, or attachment to any kind of mounting fixture. The base member 22 of the orthodontic appliance 10 has a tooth-facing surface (not shown) which is preferably conventionally concavely curved to match the natural convexity of the tooth labial surface, but other curvatures can be used to accommodate lingual bracket positioning. There are several means and methods for mounting the orthodontic appliance 10 to the tooth labial surface which are well known to persons of ordinary skill in the art and therefore will not be described herein.

Figure 2:
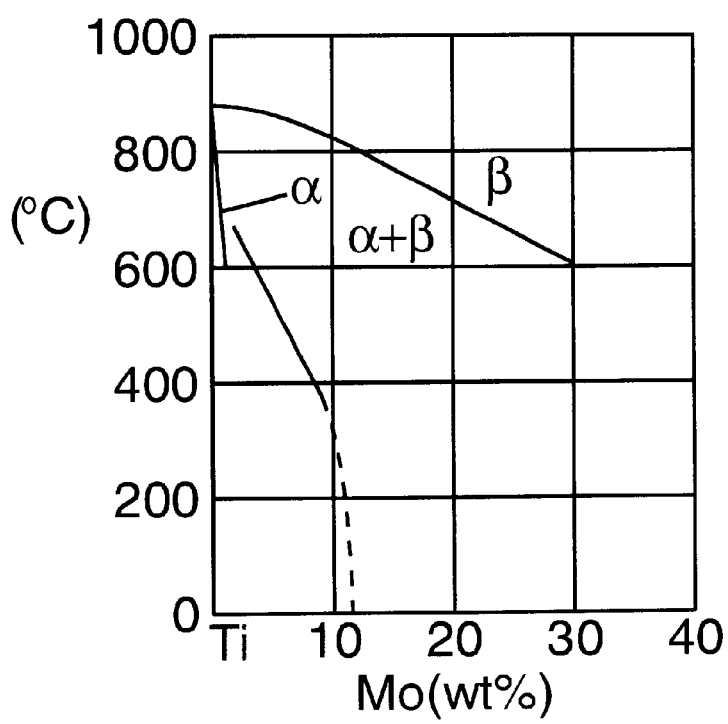
FIG. 2 is a Ti—Mo system binary phase diagram showing temperature (in °C.) as a function of wt % of molybdenum.

The orthodontic appliance 10 of the present invention preferably is formed of a titanium alloy comprising a β-stabilizing element such as molybdenum (Mo). The weight percent (wt %) of the molybdenum component of the alloy is selected so as to obtain a β-monophase that is stable at body temperature. This is accomplished by adding molybdenum at a ratio of at least 12 wt %. As shown in the Ti—Mo system binary phase diagram in FIG. 2, when β-titanium is quenched and when the Mo is maintained above 12 wt %, the β-titanium can reside at up to body temperature. The alloy shown in FIG. 2 has 15 % Mo added.

The titanium alloy according to the present invention may also comprise zirconium (Zr) as a β-stabilizing element. Preferably 5 wt % of zirconium is added to the alloy to create the desired β-stabilizing effect.

In addition to comprising β-stabilizing elements, the titanium alloy according to the present invention may also comprise aluminum (Al). Preferably about 3 wt % of aluminum is added to the alloy. Because the titanium alloy of the present invention is an age hardened β-alloy, the addition of aluminum improves the age hardenability by strengthening the α-phase. Unlike other alloys used in vivo containing an aluminum component, the aluminum of the β-titanium alloy of the present invention does not bond with inorganic phosphorus so as to lead to a deficiency of phosphorus.

Ti-15Mo-5Zr and Ti-15Mo-5Zr-3Al are examples of β-titanium alloys according to the present invention. Under STA conditions, the yield strengths of these alloys were found to be within the range 1300 to 1450 MPa. The tensile strengths of these alloys were found to be within the range 1350 to 1500 MPa. The elongations were found to be within the range 10 to 14%. Thus, the alloys according to the present invention have elongations and resistances equivalent to or better than prior compositions without causing any of the harmful effects that these prior compositions may cause in vivo.

A characteristic feature of the Ti-15Mo-5Zr alloy is its superior corrosion resistance which is a property of present importance, and it shows results superior to pure titanium even in sterilized environments and corrosive environments. Also in regard to its processability, it can be welded in an inert gas atmosphere, and there is no hardening in the welded portions or heat affected portions even when diffusion welding is done using titanium soldering, such as for bands with buccal tubes and brackets with bonding bases.

Figure 3:
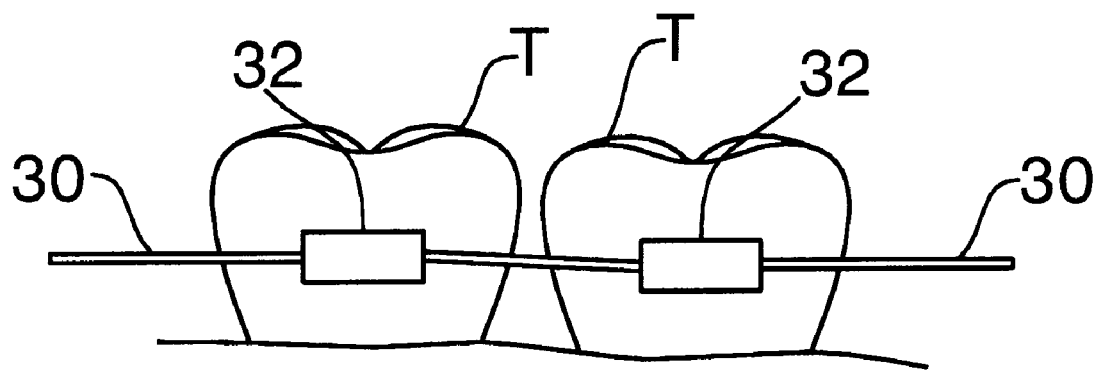
FIG. 3 is a side plan view of an archwire according to the present invention mounted to the teeth of a dental arch.

In another embodiment according to the present invention, the titanium alloys of the above examples were tested in an archwire. An exemplary archwire 30 is shown in FIG. 3. The archwire 30 is mounted to a pair of brackets 32 fastened to teeth T of a dental arch. Under STA conditions, it was found that the tensile strengths of the archwire samples were within the range 1750 to 1950 MPa. These tensile strengths are better than stainless steel piano wire.

Neither the brackets 32 nor the archwire 30 require any further description since the development of these orthodontic appliances is known and the latter differ from the known appliances only in their material compositions.

The present invention is not limited to the embodiments disclosed herein. Those skilled in the art will understand that changes and modifications in the embodiments described herein may be made without departing from the spirit of the invention. Such changes and modifications are intended to be within the scope of the invention, as defined by the claims appended hereto.

We claim:

1. An orthodontic appliance formed of a titanium alloy which substantially avoids toxic or allergic reactions in patents comprising a β-stabilizing element including at least 12 wt % molybdenum to produce a β-monophase that is stable at body temperature.

2. The orthodontic appliance according to claim 1, further comprising about 5 wt % zirconium.

3. The orthodontic appliance according to claim 1, further comprising about 3 wt % aluminum.

4. The orthodontic appliance according to claims 2 or 3, wherein the yield strength of the titanium alloy is within the range 1150 to 1450 MPa.

5. The orthodontic appliance according to claim 4, wherein the tensile strength of the titanium alloy is within the range 1350 to 1950 MPa.

6. The orthodontic appliance according to claim 5, wherein the elongation of the titanium alloy is within the range 10 to 14%.

7. An orthodontic appliance comprising:

bracket means for engaging an archwire therein, having a longitudinal slot formed in an upper surface thereof, said bracket means being formed of a titanium alloy which substantially avoids toxic or allergic reactions in patients comprising a β-stabilizing element including at least 12 wt % molybdenum to produce a β-monophase that is stable at body temperature.

8. The orthodontic appliance according to claim 7, further comprising two pairs of tie-wings carried integrally on opposite sides of said bracket means.

9. The orthodontic appliance according to claim 8, wherein the titanium alloy further comprises about 5 wt % zirconium.

10. The orthodontic appliance according to claim 8, wherein the titanium alloy further comprises about 3 wt % aluminum.

11. The orthodontic appliance according to claims 9 or 10, wherein the yield strength of the titanium alloy is within the range 1150 to 1450 MPa.

12. The orthodontic appliance according to claim 11, wherein the tensile strength of the titanium alloy is within the range 1350 to 1950 MPa.

13. The orthodontic appliance according to claim 12, wherein the elongation of the titanium alloy is within the range 10 to 14%.

14. An orthodontic bracket formed of a titanium alloy which substantially avoids toxic or allergic reactions in patients comprising a β-stabilizing element including at least 12 wt % molybdenum to produce a β-monophase that is stable at body temperature, the yield strength of the titanium alloy being within the range 1150 to 1450 MPa, the tensile strength of the titanium alloy being within the range 1350 to 1950 MPa, and the elongation of the titanium alloy being within the range 10 to 14%.

15. The orthodontic bracket according to claim 14, further comprising about 5 wt % zirconium.

16. The orthodontic bracket according to claim 14, further comprising about 3 wt % aluminum.

17. An archwire formed of a titanium alloy which substantially avoids toxic or allergic reactions in patients comprising a β-stabilizing element including at least 12 wt % molybdenum to produce a β-monophase that is stable at body temperature, about 5 wt % zirconium and about 3 wt % aluminum.

* * * * *